(12) United States Patent
Cox et al.

(10) Patent No.: US 6,499,843 B1
(45) Date of Patent: Dec. 31, 2002

(54) CUSTOMIZED VISION CORRECTION METHOD AND BUSINESS

(75) Inventors: Ian G. Cox, Honeoye Falls, NY (US); Howard P. Markman, Honeoye, NY (US); Kamal Sarbadhikari, Penfield, NY (US); Ronald J. Martino, Geneva, NY (US); Kristian Hohla, Vaterstetten (DE)

(73) Assignee: Bausch & Lomb Incorporated, Rochester, NY (US)

( * ) Notice: Subject to any disclaimer, the term of this patent is extended or adjusted under 35 U.S.C. 154(b) by 81 days.

(21) Appl. No.: 09/661,028

(22) Filed: Sep. 13, 2000

(51) Int. Cl.7 ................................................. A61B 3/00
(52) U.S. Cl. ...................................................... 351/246
(58) Field of Search ................................. 351/205, 206, 351/211, 212, 41, 246, 247, 219; 128/898

(56) References Cited

U.S. PATENT DOCUMENTS

| | | | |
|---|---|---|---|
| 4,669,466 A | 6/1987 | L'Esperance | 128/303 |
| 4,923,467 A | 5/1990 | Thompson | 623/5 |
| 5,179,262 A | 1/1993 | Portney et al. | 219/121.68 |
| 5,240,553 A | 8/1993 | Jones | 156/643 |
| 5,452,031 A | 9/1995 | Ducharme | 351/177 |
| 5,460,627 A | 10/1995 | O'Donnell, Jr. | 606/4 |
| 5,777,719 A | 7/1998 | Williams et al. | 351/212 |
| 5,841,511 A | 11/1998 | D'Souza et al. | 351/212 |
| 5,891,132 A | 4/1999 | Hohla | 606/5 |
| 5,926,247 A * | 7/1999 | Kimura | 351/41 |
| 5,949,521 A | 9/1999 | Williams et al. | 351/246 |
| 6,050,687 A * | 4/2000 | Bille et al. | 351/212 |
| 6,086,204 A | 7/2000 | Magnante | 351/212 |
| 6,095,651 A | 8/2000 | Williams et al. | 351/246 |

OTHER PUBLICATIONS

An US Pub. No. 2002/0062255A1 Entitled "Method of Selling Contact Lens" published May 23, 2002 to Tanaka, et al.

* cited by examiner

*Primary Examiner*—George Manuel
(74) *Attorney, Agent, or Firm*—William Greener

(57) ABSTRACT

A method and business architecture for providing vision correction to a patient involves obtaining wavefront aberration measurement information and, optionally, patient history data, ordering data, dispensing data, billing data, and other information, from the patient; transmitting the various data to respective appropriate platforms, e.g., transmitting the wavefront aberration information to a custom lens supply platform; producing a custom lens for the patient; and delivering a custom lens to the patient in a personalized manner. The method further involves fitting and measurement processes including in-situ lens shaping and custom manufacture of contact lenses, IOLs, inlays or onlays by laser ablation, lathing, casting/molding and machining. Business architectures according to the invention include segregating vision correction method steps into contractual, revenue generating business transactions.

59 Claims, 8 Drawing Sheets

CUSTOMIZED VISION CORRECTION METHOD AND BUSINESS

BACKGROUND OF THE INVENTION

1. Field of the Invention

The present invention relates to the field of vision correction and, more particularly, to methods and devices for providing customized vision correction, and business methods associated with providing such correction.

2. Description of Related Art

A large portion of the population is ametropic; i.e., their vision is less than optimum due at least in part to refractive abnormalities of the eye. For over 100 years, practitioners ranging from lens fitters to surgeons have engaged in the business of providing vision correction to the ametropic population, as technology permitted, through spectacles; more intimate devices such as contact lenses, intra-ocular lenses (IOLs), inlays and onlays; and via surgical procedures including cataract removal, keratoplasty (corneal replacement), variations of keratotomy such as RK (radial keratotomy), PRK (photorefractive keratotomy) and other refractive surgical procedures the most popular of which currently is LASIK (laser assisted in-situ keratomileusis). In general terms, LASIK involves sculpting the cornea of the eye with an excimer laser to give it a shape that results in better vision for the patient.

While spectacles, contact lenses, and the like generally help people see better, it is widely known that conventional vision correction devices and procedures still do not and cannot correct all refractive error. This is due in part because traditional vision correction only addresses a few of the many aberrations that cause less than perfect vision, and further in part because treatments such as LASIK tend to introduce certain aberrations at the same time that they greatly reduce some of the more gross refractive errors. Thus, after successful LASIK treatment, a person may no longer find it necessary to wake up in the morning with eyeglasses in hand to find their slippers, however, they may experience other visual annoyances associated, for example, with nighttime vision.

Relatively recent advances in ophthalmologic technology are being developed and refined to address the aforementioned issues. Sophisticated instruments such as the Orbscan™ m ocular topography system by Orbtek, Inc. and wavefront sensing devices for measuring and correcting higher-order aberrations such as that disclosed in Williams et al. U.S. Pat. No. 5,777,719, the disclosure of which is herein incorporated by reference in its entirety, provide tools to evaluate residual refractive errors and, when used in conjunction with advanced laser systems like the 217C laser system manufactured by Technolas GmbH, and other eye care technology, have the potential to provide supernormal vision.

Concomitant efforts are directed to incorporate these technological advances into business architectures that can deliver enhanced value to practitioners, vendors, consumers, and patients be it in the form of economic, social, or personal enhancement.

SUMMARY OF THE INVENTION

A solution that addresses the issues and concerns identified above is set forth by the present invention. The term "vision correction" as used in the description of the invention refers both to a measured improvement in vision over that provided by conventional refractive correction and to the subjective evaluation of "seeing better" by the patient. The term "practitioner" as used herein refers appropriately to anyone qualified to fit, prescribe, or dispense vision correction devices such as spectacles and the like, or medically attend to a patient particularly with respect to the patient's eyes.

In accordance with the purpose of the invention, as embodied and broadly described herein, a method for providing vision correction to a patient involves engaging the patient in a practitioner's facility; obtaining an ocular wavefront aberration measurement from the patient in the practitioner's facility; transmitting the wavefront aberration measurement and other associated data including patient and practitioner information in suitable form to a custom lens supply platform and other platforms as appropriate; manufacturing a custom lens at the supply platform; and providing the patient or the practitioner with the custom lens. In the instant embodiment, the custom lens may be a contact lens, an inlay, an onlay, or an IOL. In this and the embodiments to follow, the custom lens supply platform provides for manufacturing the appropriate custom lens preferably, but not necessarily, at a location remote from the practitioner's facility by known manufacturing methods. These methods include, but are not limited to, laser ablation, lathing, cast-molding, or otherwise machining a lens surface. Moreover, in this and the embodiments to follow, the wavefront aberration measurement is preferably obtained with a wavefront sensor but may alternatively or complementarily be obtained by phase diversity techniques, ocular topography, pachymetry and other suitable means known to those skilled in the art for obtaining wavefront aberration information. The measured wavefront aberrations preferably refer to third and higher-order aberrations and, more preferably, to fifth to tenth order aberrations, but are not limited as such. In an aspect of this embodiment, the steps of obtaining an ocular wavefront aberration measurement from the patient in the practitioner's facility; transmitting the wavefront aberration measurement and associated data to a custom lens supply platform; and manufacturing a custom lens at the supply platform are segregated into respective businesses, any or all of which may carry contractual rights for practice and, further, any or all of which may be the source of a royalty or other income. The contractual rights may be exclusive or non-exclusive and may be granted to any number of parties. In another aspect of this embodiment, practice of the invention will provide the patient with vision correction and resulting visual performance from the custom lens that is better than that which would be provided to the patient from a conventional refraction.

A related embodiment of the invention for providing vision correction involves engaging a patient in a practitioner's facility where the patient is fitted with a trial contact lens having a non-customized anterior surface shape; identifying, by a mark or non-contact means, the geometric center of a surface of the trial lens; obtaining a wavefront aberration measurement from the patient's eye along an eye axis passing through the geometric center of the lens; transmitting the aberration measurement in an appropriate form to a custom contact lens supply platform; and manufacturing a custom contact lens for the patient.

In another embodiment according to the invention for providing vision correction, a patient is engaged in a practitioner's facility; the patient is fitted with a trial lens having a non-customized anterior surface shape; a wavefront aberration measurement is obtained from the patient's eye with the trial lens in place; the aberration measurement information is transmitted in suitable form to a device adapted for custom-shaping the anterior lens surface; and the anterior lens surface is custom shaped in-situ by the device. In this embodiment, the lens may be a contact lens, an onlay, or an inlay. The in-situ custom shaping would preferably be by laser ablation. In an aspect of this embodiment, the aberration measurement information is also transmitted in suitable form to a custom lens supply platform where a custom lens is made for the patient. In another aspect of this embodiment, fitting the patient with the trial lens further involves identifying, by a mark or non-contact means, the geometric center of a surface of the trial lens and obtaining the wavefront aberration measurement along an eye axis passing through the geometric center of the lens. In some individual cases, it may be preferable to dilate the patient's pupil to cover an appropriate portion of the optical zone of the trial lens.

Another embodiment of the invention provides a method for vision correction including engaging the patient in a practitioner's facility; obtaining a wavefront aberration measurement of the patient's eye; and providing a display of the wavefront aberration measurement in the form of either a picture, a computer simulation, a graphic display, and/or a mathematical representation of the wavefront. In a preferred aspect of this embodiment, the display is in a form that allows the patient to make a subjective evaluation of the wavefront aberration measurement which will lead to the subjective evaluation of better vision. A related aspect involves transmitting the wavefront measurement to a lens supply platform in a form readable by the lens supply platform for producing a custom lens.

In a related embodiment, obtaining the wavefront aberration measurement of the patient's eye including presenting a display of the measurement to the patient may be accomplished automatically outside of a practitioner's facility, in similar fashion, for example, to obtaining blood pressure readings from devices located in supermarkets, workplaces, etc. The desired information could then be transmitted automatically to a practitioner (e.g., for diagnostic purposes) or to a custom lens supply platform for making lenses for the patient if desired.

In another related embodiment, a method for providing vision correction to a patient involves measuring an ocular characteristic of the patient's eye, either by a practitioner in the practitioner's facility or remotely without practitioner intervention. The measurement includes topography data and/or wavefront aberration data. This measured data is evaluated and the evaluation produces an option matrix that compares, among other things, prospective vision correction as a function of a prospective eye treatment, cost of treatment options, etc. Based upon the evaluation, the patient can select her treatment option, and billing and lens manufacturing can occur automatically upon selection.

In an aspect suited to all of the embodiments described above, patient data may also be supplied to an appropriate location or platform to accommodate, e.g., record keeping, ordering, billing, and delivery information, building and maintaining patient databases, treatment surveys, for economic and productivity evaluations, etc. Any of the embodiments are also amenable to automated billing via, e.g., credit/debit card services. The interactive aspects of the invention provide for a "semi-intelligent" system in that it facilitates database feedback to interested parties. This kind of information allows real-time choice options to be evaluated by the patient, the practitioner, manufacturers and other interested parties.

It will be appreciated by those skilled in the art that any data transmission referred to above could be in the form of telecom or datacom, and could be sent via wire-based (optical fiber, cable, etc.) or wireless services. A preferable interface would be Internet based.

BRIEF DESCRIPTION OF THE DRAWINGS

The accompanying drawings, which are incorporated in and constitute a part of this specification, illustrate embodiments of the present invention and, together with the description, serve to explain the objects, advantages and principles of the invention. In the drawings.

DETAILED DESCRIPTION OF THE PREFERRED EMBODIMENTS

Figure 1:
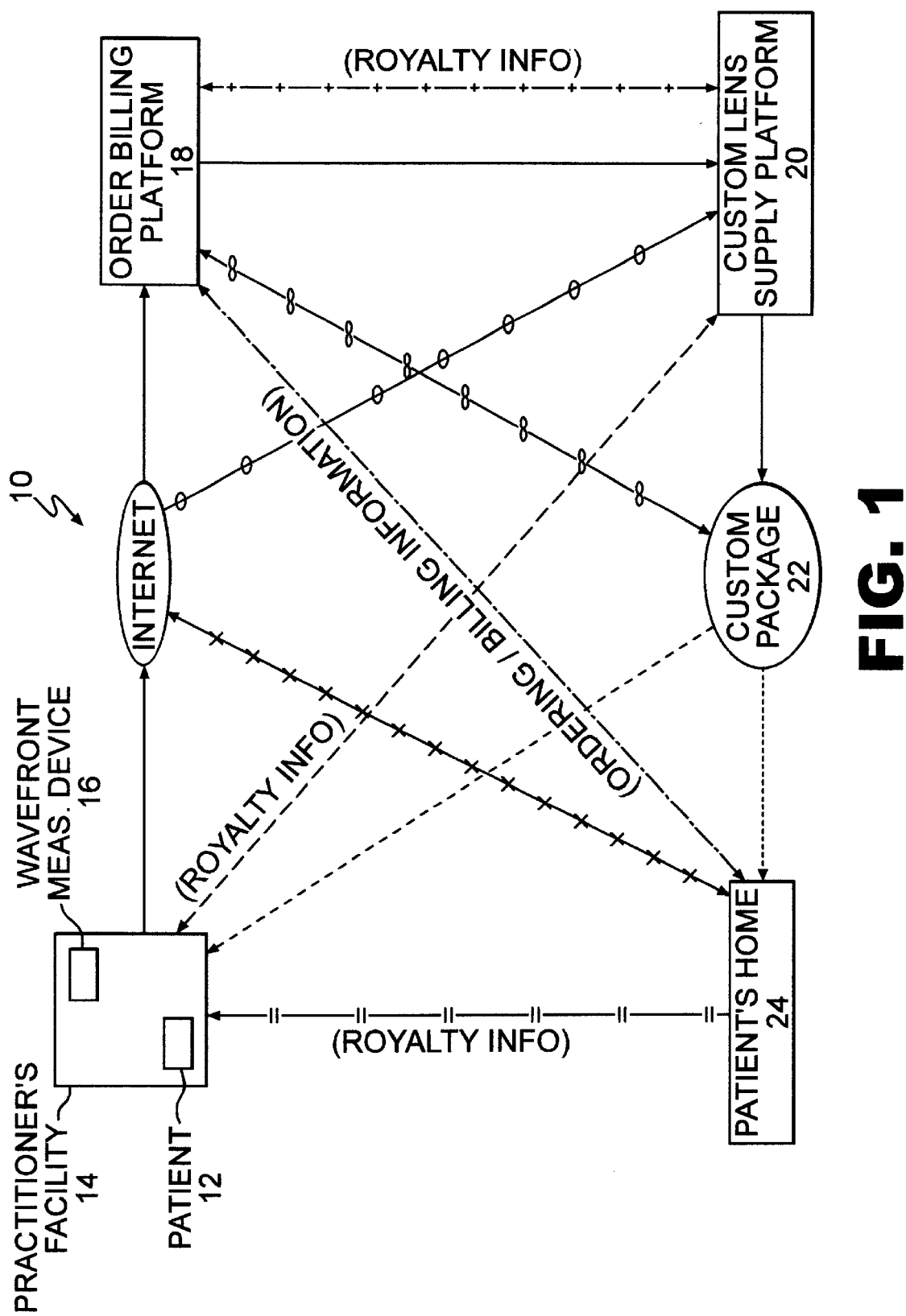
FIG. 1 is a block view of an exemplary business architecture for providing a custom lens to a patient according to an embodiment of the invention.
Figure 4:
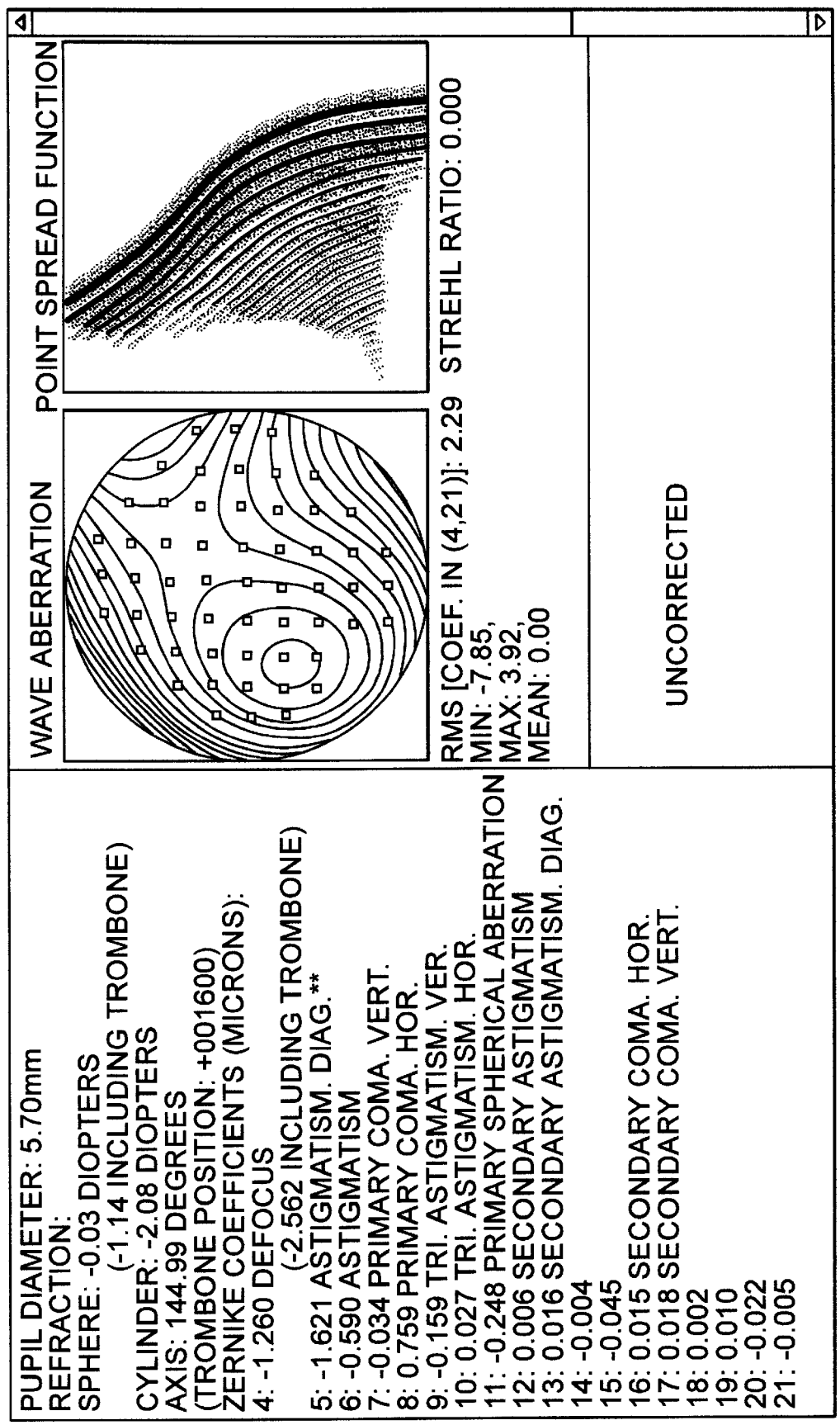
FIG. 4 is a representative display of a sample patient's wavefront aberration measurement before correction of higher-order aberrations.
Figure 6:
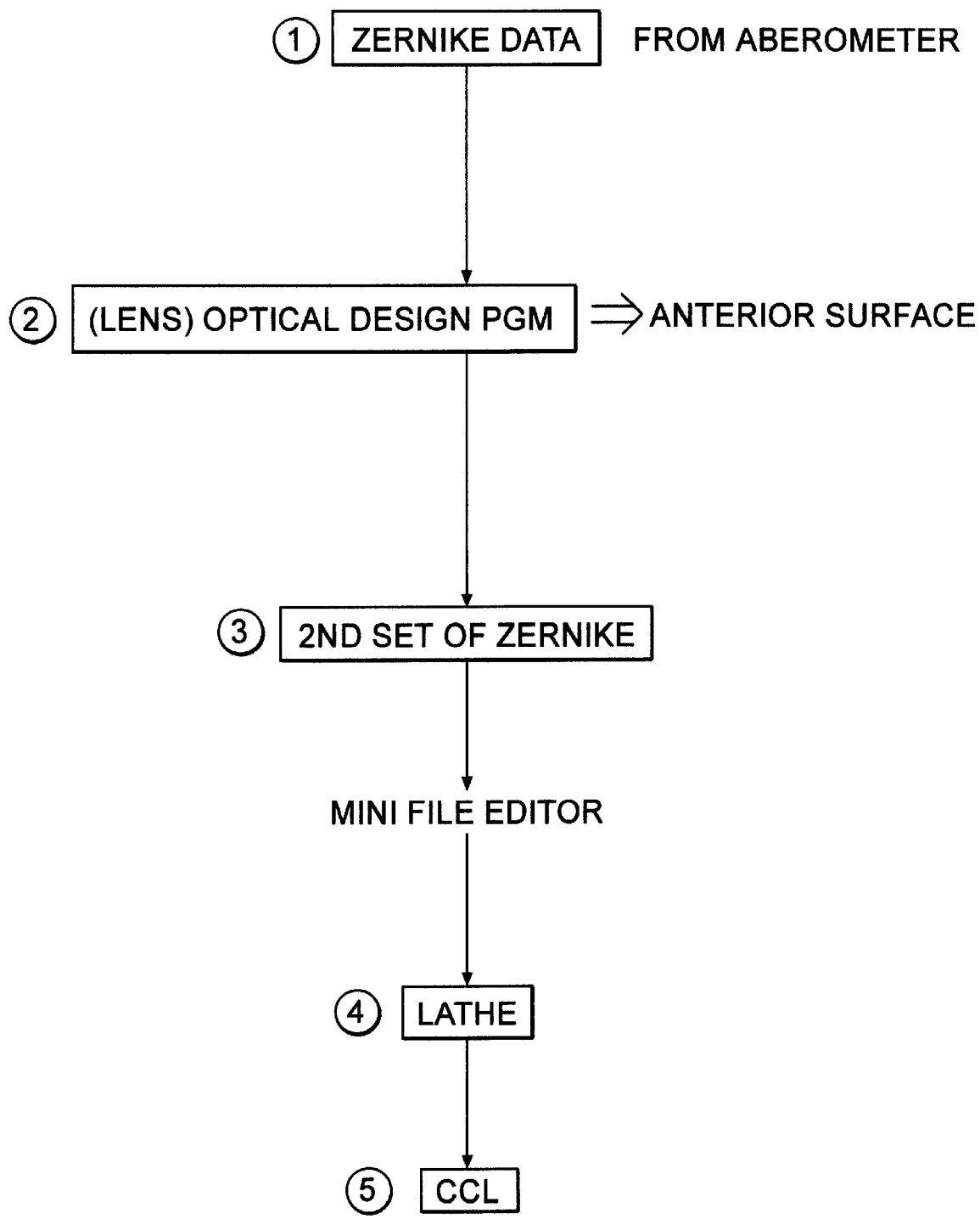
FIG. 6 is a flowchart of a representative method according to an embodiment of the invention.

An exemplary business architecture 10 is illustrated in FIG. 1 in accordance with a preferred embodiment of providing vision correction to a patient 12. The patient 12 presents herself at a practitioner's facility 14. The practitioner's facility is suitably equipped with apparatus (not shown) for obtaining, in particular, wavefront aberration information 16 from the patient. The apparatus is preferably one of a variety of wavefront measuring instruments (e.g., Zywave™ wavefront aberration sensor from Bausch & Lomb Surgical/Technolas, Munich) or other suitable devices and associated procedures for obtaining wavefront aberration information such as, e.g., phase diversity and/or topography. FIG. 4 is an exemplary display of a patient's wavefront aberration information. This information may take a variety of forms which are most suitably useable by a practitioner for diagnosis, prescribing, etc.; by the patient for informed consent, information, subjective evaluation, etc.; by an ordering and/or billing platform 18, and particularly, for a custom lens supply platform 20 where a custom lens based upon the wavefront measurement information can be made and packaged for shipment to the practitioner or the patient. In addition, other refractive data and patient data may be obtained and transmitted. As such, different platforms may be interconnected. The selected diagnostic equipment is preferably designed to automatically output the appropriate information in suitable form to the custom lens supply platform 20. It is well known in the art how to convert a wavefront measurement into data that a laser, lathe or other suitable surface modifying equipment can use to create a desired surface modification; therefore, that exercise need not be discussed at length herein, nor does it constitute a material part of the invention described herein. For illustration, however, an exemplary process is shown with reference to FIG. 6. FIG. 6 is a flow chart of an exemplary aspect of the invention for a custom contact lens produced by lathing. Starting at block 1, Zernike polynomial data is output by a wavefront measuring apparatus. The data is input at block 2 to an optical design program that in its most basic capacity designs the shape of the anterior surface (optical zone and/or peripheral zone) of the proposed contact lens. A second set of Zernike data is generated at block 3. This data is preferably in the form of a mini-file or other suitable format that is readable by a lens turning lathe. The mini-file data is input into the lathe processor at block 4 and a custom contact lens is produced at block 5. Referring again to FIG. 1, as illustrated, some information is transmitted from one platform to another platform via the Internet, however, any supporting transmission mode and transmission medium can be used. It is contemplated that some or all of the platforms will be located remote from the practitioner's facility but this need not be so.

Figure 7:
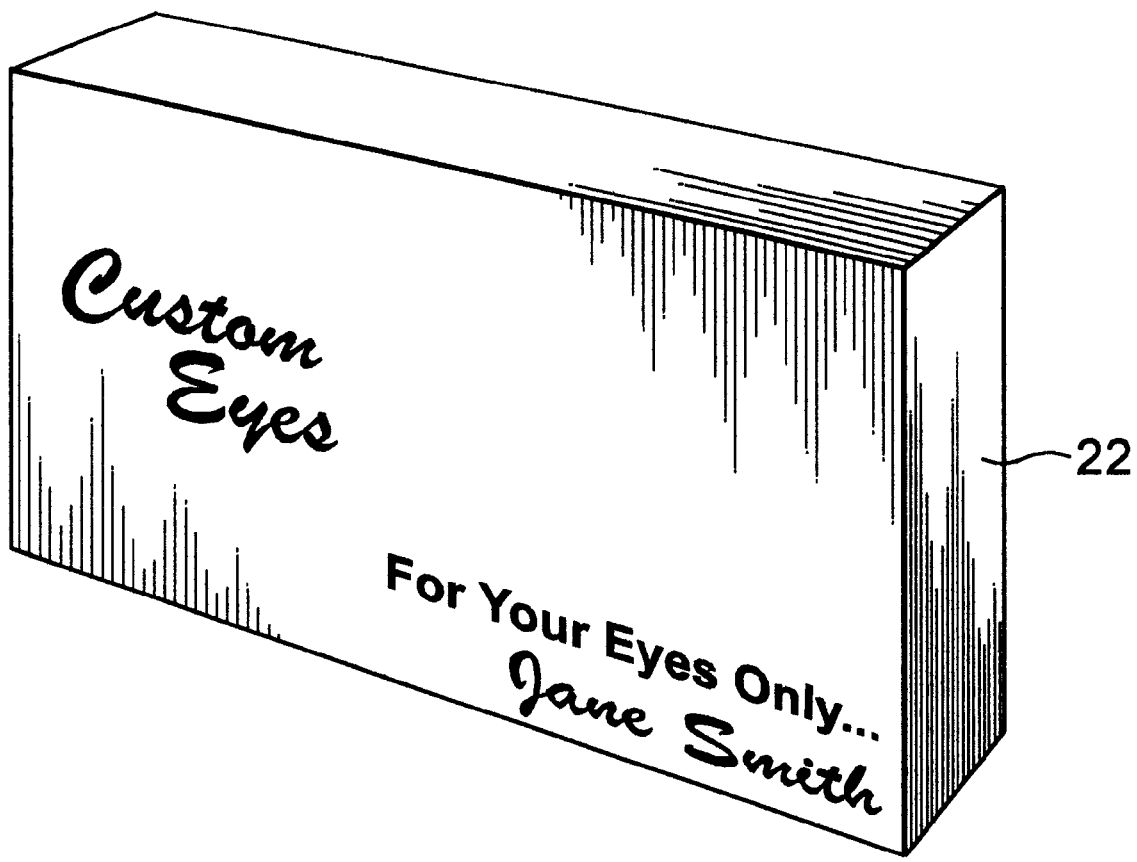
FIG. 7 is a picture of an exemplary custom lens container for delivery to a patient.

The supply platform 20 is suitably equipped to produce an appropriate custom lens. Accordingly, a custom contact lens, a custom inlay, a custom onlay, or a custom IOL can be made. The manufacturing process will preferably entail shaping a surface of the custom lens. This may be accomplished by one or more of the processes including laser ablation, lathing, casting/molding, or other known processes. A specific quantity of custom lenses, e.g., contact lenses, may be produced for the patient so as to be used over an extended period of time. The lenses will preferably be packaged in a customized manner 22 (as they are custom lenses) for the patient. An exemplary representation of a customized package is shown in FIG. 7. The package can then be shipped to the patient or practitioner as appropriate.

Figure 5:
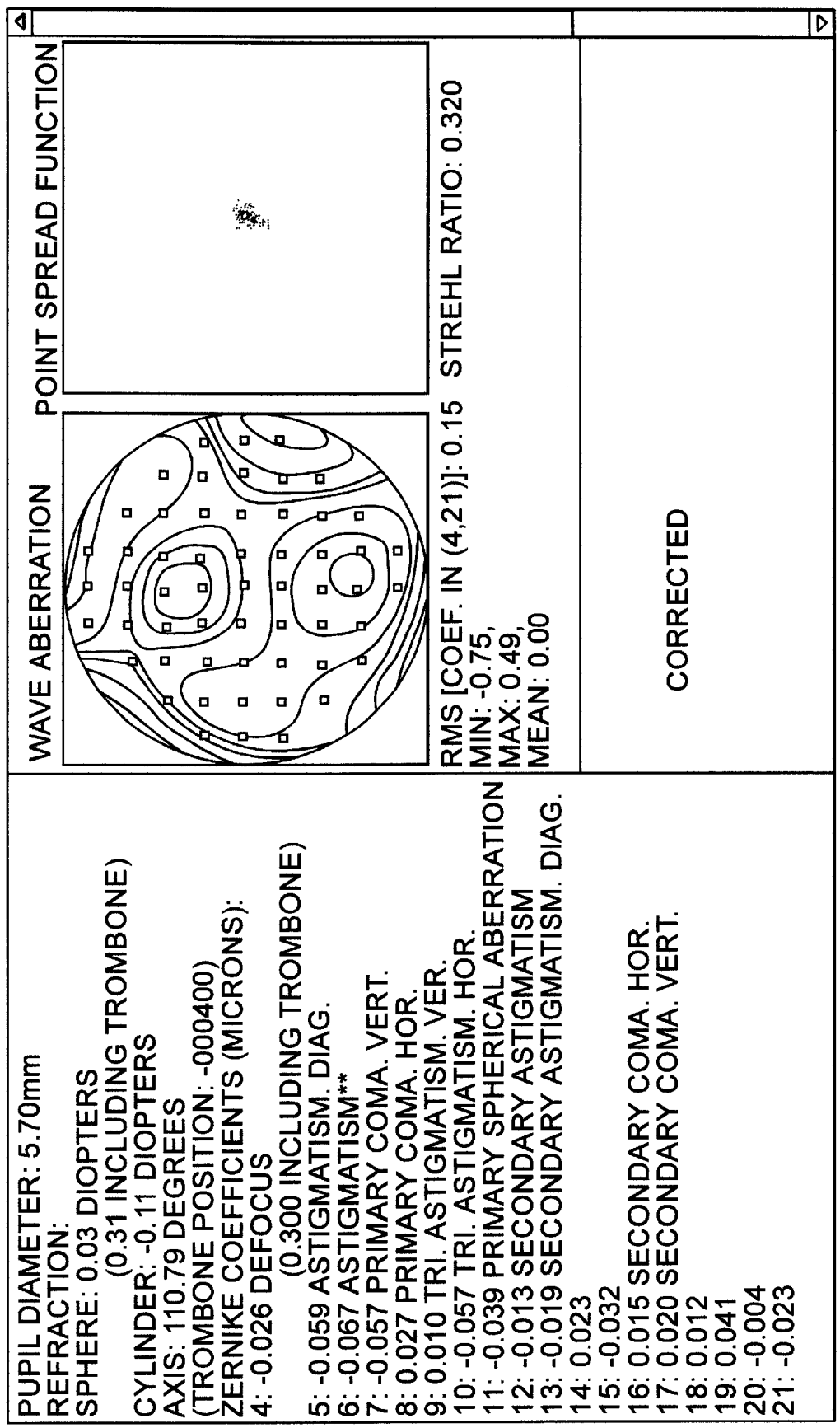
FIG. 5 is a representative display of a sample patient's wavefront aberration measurement after correction of higher-order aberrations.

In an aspect of the embodiment, it may be desirable to show the patient, to the extent possible, what their improved vision could be as provided by the custom lens. An instrument much like a wavefront sensor device equipped with a phase compensator such as a deformable mirror, as shown in U.S. Pat. No. 5,777,719, can provide an indication of wavefront corrected vision. An exemplary aberration corrected wavefront display is shown in FIG. 5 resulting from the corrected wavefront aberrations shown in FIG. 4.

It will be appreciated that the customization aspect of the present invention is primarily attributed to the measurement and correction of higher-order wavefront aberrations. These are generally considered to consist of monochromatic aberrations associated with third and higher order Zernike polynomials and particularly fifth to tenth order Zernike modes.

An exemplary business practice used in the laser vision correction industry involves per procedure fees. This practice is illustrated by the sale of non-reusable laser interlock cards to the doctor that were inserted into the laser and, without which, the laser would not operate. This model is also appropriate, for example, as applied to obtaining a wavefront aberration measurement. It is envisioned that a per use fee may be implemented each time the wavefront sensor is used to obtain aberration information. Likewise, any of the processes constituting portions of the method of the invention, particularly those occurring between different or third party-controlled platforms, may be crafted as business activities that carry a royalty or other income generation for their use. Accordingly, it is contemplated to automatically transmit various data and information between platform constituents for this purpose with an intent of enhancing the value of the products and/or services provided. Part of this enhanced value stream includes improved vision to the patient exceeding the improvements expected or obtained over conventional refraction practice, and enhanced value to the practitioner.

Figure 2:
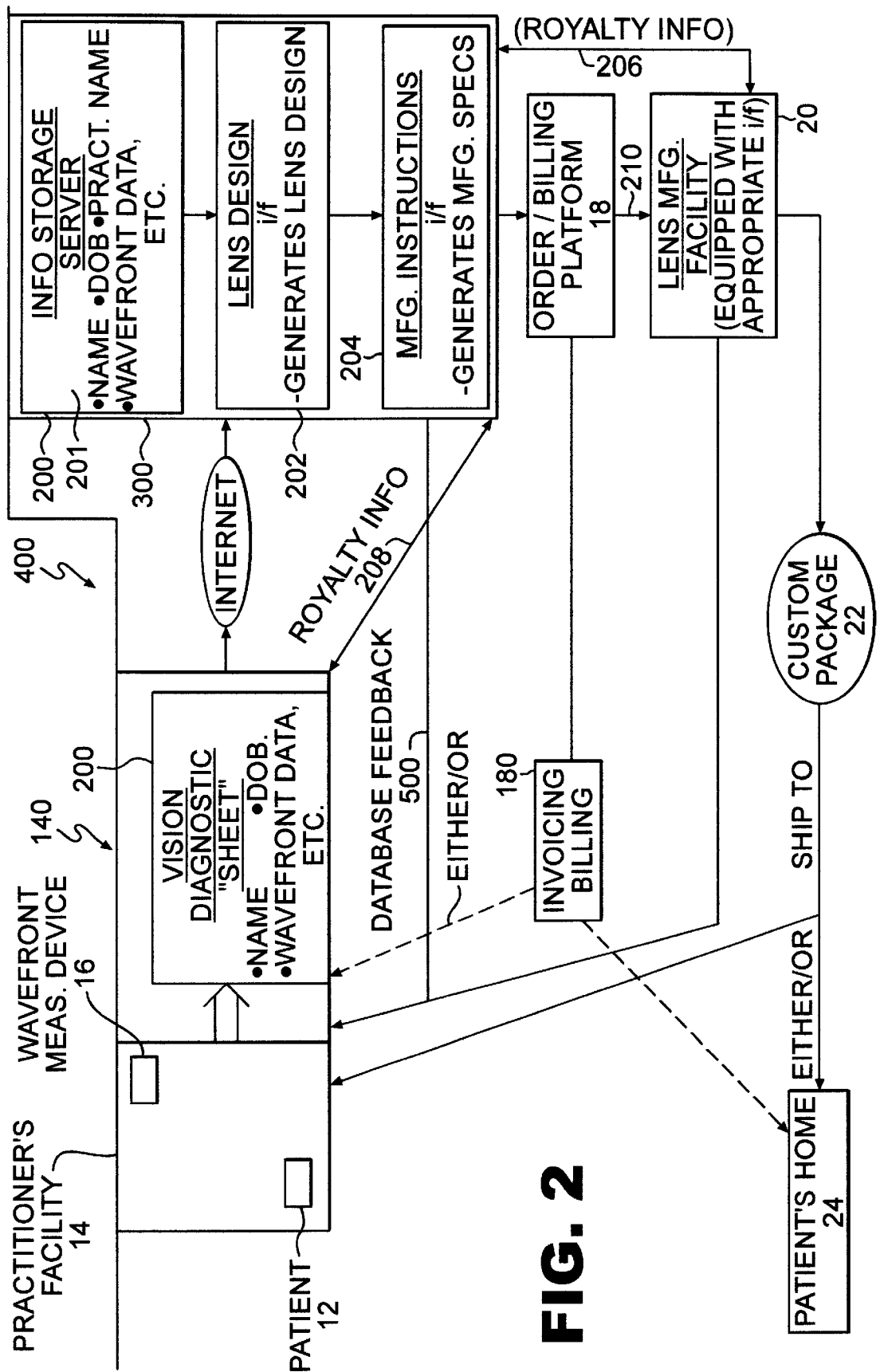
FIG. 2 is a block view of an alternative aspect of a business architecture for providing a custom lens to a patient according to an embodiment of the invention.

FIG. 2 is a block diagram illustrating an alternative business architecture 400 to that shown in FIG. 1, and is the basis of a semi-intelligent interactive system. A practitioner's platform 140 comprises the practitioner's facility 14 where the patient 12 is engaged to generate vision diagnostic information 200, including wavefront measurement data, personal history, practitioner information and whatever other information may be useful for constructing or maintaining one or more databases for future use. The vision diagnostic information 200 is sent via the internet to a service platform 300 that illustratively includes an information storage server 201, a lens design interface 202, and a lens manufacturing interface 204. Two types of information are generated from service platform 300: order, billing, and optional demographic information, 180, for example, are sent to and received by an order/billing platform 18; and lens design and manufacturing information 210 is sent to and received by a custom lens platform 20. Ordering/billing information 180 can be transmitted to the practitioner, the patient, or both. Custom lens information 210 is used by lens platform 20 to produce custom packaged lens products 22 for the patient which can be shipped to the patient at home 24, for example, or to the practitioner's facility 14 for fitting and/or delivery to the patient 12. Simultaneous to the transfer of patient and lens information 180, 210, respectively, various royalty information 206, 208, may be transmitted between various platforms, for example, as shown. Moreover, the illustrated architecture 400 may be considered a semi-intelligent interactive system in that the system provides for database feedback in real time between various platforms. For example, based upon the patient's wavefront measurement and/or other vision data and/or demographic information, the service platform 300 and/or the lens platform 20 and/or the billing platform 18 may generate feedback 500 to the practitioner and/or the patient that influences the decisions about type of treatment, type of lens, quantity, payment, etc. To illustrate this, a patient may seek to obtain vision correction (or improvement) by laser vision correction. Certain ocular characteristics of the patient will be measured, preferably wavefront aberration and possibly, in conjunction therewith, topography measurements will be obtained. A practitioner or, alternatively, a computer determined evaluation, for example, may conclude that the patient's prospective vision correction could be better accomplished not by laser vision correction but, foe instance, by a custom contact lens. The evaluation may be in the form of an option matrix so to speak wherein information about prospective vision correction and cost, among other things, can be compared against different types of eye treatment or no treatment at all. An eye treatment option can then be selected by the patient and/or the practitioner, and upon selection, the appropriate information such as wavefront aberration data and patient financial information, for example, can be automatically sent to the appropriate platform (in the illustrated case, a custom lens supply platform and an order/billing platform, respectively) for processing.

In another embodiment of the invention for providing vision correction to a patient, the patient situates himself in a practitioner's facility. At the facility, a diagnostic lens is selected and fitted to the eye. The diagnostic lens will be of similar design to that which will eventually be prescribed as the custom contact lens. The power of the lens preferably should be spherical (defocus) only, similar in magnitude to that of the patient's eye. However, if the patient's spherical power is not known, a standard plano powered lens could be used. Base curve selection is based on central corneal curvature readings made with a keratometer or a corneal topographer. If neither is available, the trial lens can be fitted empirically by observation of the movement, centration and rotation of the lens. Regardless of the methodology used to select the lens, the lens is placed on the eye, allowed to equilibrate for up to 10 minutes, and then the centration, movement and rotation is assessed using a biomicroscope. The lens should show movement when blinking but remain relatively stable between blinks. Ideally it should return to its primary gaze position between blinks, with little variation in horizontal or vertical centration. If excessive movement or decentration is present, a steeper base curve diagnostic lens should be fitted. The patient's wavefront will then be measured with the diagnostic lens in place. Ideally, the patient will have a large pupil (greater than 5 mm) under the illumination conditions that the wavefront is measured. If the conditions are not such that the patient's pupil is dilated to 5 mm naturally, then a pharmacological agent may be instilled to ensure adequate pupil size under the illumination conditions used for wavefront measurement. By correcting the patient's wavefront over a large pupil size, the patient would be wavefront corrected over a wide range of pupil sizes, and pupillary axes, since this axis shifts in many patients in relation to pupil size. Measurement in this fashion eases lens fabrication since some methods of manufacture, particularly those which are lathe based, are easier to control if the optical surface is centered symmetrically on the lens. The wavefront measurement should be made along the geometric central axis of the lens, this axis being defined by viewing the edge of the lens or by viewing particular marks made on the diagnostic lens which define the geometric center of the lens (e.g. a circle) while viewing the lens through a camera mounted in the wavefront sensor instrument. Using a Hartmann-Shack type aberration sensor, an image of the lenslet array images is captured on the wavefront sensor CCD camera, and converted by software algorithms into a series of Zernike coefficients which describe the wavefront aberration of the eye and diagnostic lens system. If so equipped, the rotation of the diagnostic lens on the eye will be measured by the wavefront sensor, by sensing of specific marks made on the diagnostic lens and capturing an image of the lens in its stable primary gaze position with the camera mounted in the wavefront sensor instrument. If this capability is not available, the clinician will measure the rotation of the lens on the eye using an eyepiece reticle, and the specific marks of the diagnostic lens. In an alternative aspect of this embodiment for measuring wavefront aberrations along an axis passing through the geometric center of the lens, an axis shift is introduced. Once the resting position of the trial (diagnostic) lens on the patient's eye is determined, the patient's visual axis is aligned to the measurement axis of the metrology system, preferably an aberration sensor. This is typically a self-alignment by the patient accomplished by looking at a target presented by the metrology system. The measurement axis is then shifted from the visual axis to a parallel axis that passes through the geometric center of the lens. This can be accomplished by the operator of the aberrometer by shifting the optical axes of the pupil camera and wavefront sensor to an axis that is parallel to the visual axis of the patient and passes through the center of the trial lens. The pupil camera and wavefront sensor are conveniently mounted on the same X-Y translation stage such that they are moved in unison. The geometric center of the diagnostic lens is now the reference feature for the wavefront aberration when the lens is in the resting position on the patient's eye. Optical modification to the trial lens can now be made with respect to its geometric center by any of the techniques disclosed herein. The Zernike coefficients are then converted into another series of Zernike coefficients describing the corrective lens surface for the custom contact lens. The corrective surface can be anterior of posterior on the lens. The corrective lens' Zernike coefficients can be derived by dividing the original Zernike coefficients by n−1, where n represents the refractive index of the contact lens material. All Zenike coefficients can then be multiplied by −1 to flip the z axis and make it a correcting wavefront. Alternatively, ray tracing techniques using a commercially available ray tracing pattern can be used to determine the correcting surface wavefront and hence the Zernike coefficients. The correcting surface Zernike coefficients are entered into a software program designed to produce lathing instructions for a 3-axis or similar lathe which will make the correcting surface on the customized contact lens. Alternatively instructions may be derived to guide a small beam laser designed to alter a surface of a contact lens. In both cases, the rotation of the lens on the eye is considered and included in the calculations when deriving the correcting surface Zernike coefficients. This conversion of measured Zernike coefficients and lathing instructions can be performed in a computer attached to the wavefront sensor, or remotely in a computer communicating with the wavefront sensor and transmitted to a custom lens supply platform similar to that described with respect to the foregoing embodiment. The finished lens is transported to the patient and tested.

An exemplary embodiment is described as follows:
A diagnostic lens having the parameters listed in Table I was selected and placed on the patient's eye.

TABLE I

| | |
|---|---|
| BVP: | −2.00 |
| Diameter: | 14.0 mm |
| Base Curve: | 8.3 mm Monocurve |
| Optic Zone: | 8.00 mm |
| Center Thickness: | 0.090 mm |
| Design: | On Center Front Surface PeriBallast Material: 45% water, hefilcon B |

After the lens had settled, a wavefront measurement was made with the lens in place. The measurement was centered on the geometric center of the lens. The wavefront analysis provided the Zernike coefficients listed in Table II.

TABLE II

| | |
|---|---|
| Z4 | 2.044 |
| Z5 | −0.443 |
| Z6 | 0.556 |
| Z7 | 0.292 |
| Z8 | −0.142 |
| Z9 | −0.224 |
| Z10 | −0.008 |
| Z11 | −0.250 |
| Z12 | −0.048 |
| Z13 | 0.054 |
| Z14 | −0.012 |
| Z15 | −0.104 |
| Z16 | 0.039 |
| Z17 | −0.048 |
| Z18 | 0.071 |
| Z19 | 0.063 |
| Z20 | −0.006 |
| Z21 | −0.029 |

Figure 8A:
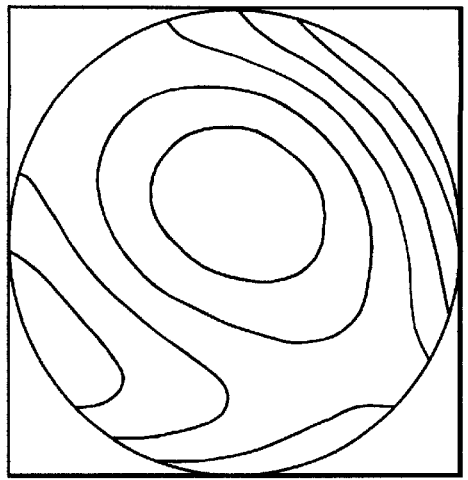
FIGS. 8A, 8B are actual wavefront and point spread function displays for a diagnostic lens and a custom contact lens according to an exemplary embodiment of the invention.

Analysis of the Point Spread Function (PSF) excluding the Z4, Z5 & Z6 terms (i.e., defocus and astigmatism) revealed a Strehl ratio for the 5.7 mm pupil over which the data was calculated to be 0.03536, as illustrated in FIG. 8A. The wavefront data was converted using a commercially available ray tracing program (e.g., ZEMAX Optical Design Software from by Focus Software, Inc., Tucson, Ariz.) to determine the Zenike coefficients for the appropriate correcting lens. They are listed in Table III.

TABLE III

| | |
|---|---|
| Zernike Term 4: | −3.4254044e-005 |
| Zernike Term 5: | 0.005762738 |
| Zernike Term 6: | −0.0045488358 |
| Zernike Term 7: | −0.0032402149 |
| Zernike Term 8: | −0.0037653647 |
| Zernike Term 9: | −0.0059788634 |
| Zernike Term 10: | −0.00411332 |
| Zernike Term 11: | 0.0030430632 |
| Zernike Term 12: | −0.0008569811 |
| Zernike Term 13: | 0.00046893498 |
| Zernike Term 14: | −0.0025860833 |
| Zernike Term 15: | 0.00083158948 |
| Zernike Term 16: | 0 |
| Zernike Term 17: | 0.00028702493 |
| Zernike Term 18: | −0.0025791693 |
| Zernike Term 19: | −0.0023277366 |
| Zernike Term 20: | −0.00011755441 |
| Zernike Term 21: | 0 |
| Zernike Term 22: | 0 |
| Zernike Term 23: | 0 |
| Zernike Term 24: | 0 |
| Zernike Term 25: | 0 |
| Zernike Term 26: | 0.0029179957 |
| Zernike Term 27: | 0.0020611676 |

(Note that the Zernike terms in Table II have been converted to the ZEMAX Zernike convention. Hence the Z term numbers in Table III do not necessarily correspond to those in Table II above or Table IV below). The custom contact lens was manufactured with the same relevant parameters as the diagnostic lens listed in Table I. The lens was placed on the patient's eye and re-measured with the wavefront sensor, producing the set of Zenike coefficients listed in Table IV.

TABLE IV

| | |
|---|---|
| Z4 | 1.852 |
| Z5 | 0.395 |
| Z6 | 0.025 |
| Z7 | −0.125 |
| Z8 | −0.368 |
| Z9 | −0.050 |
| Z10 | 0.180 |
| Z11 | −0.068 |
| Z12 | −0.096 |
| Z13 | 0.050 |
| Z14 | 0.119 |
| Z15 | −0.063 |
| Z16 | −0.097 |
| Z17 | −0.015 |
| Z18 | −0.068 |
| Z19 | 0.062 |
| Z20 | −0.008 |
| Z21 | −0.140 |

Figure 8B:
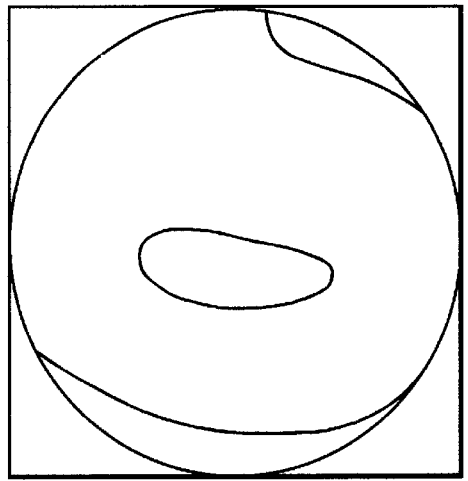

The defocus and astigmatism were not properly corrected by the lens on the eye due to an error in the actual power of the trial lens which was discovered later. However, analysis of the PSF excluding the Z4, Z5 & Z6 terms (i.e., defocus and astigmatism) revealed a Strehl ratio for the 5.7 mm pupil over which the data was calculated to be 0.09214, as shown in FIG. 8B. The Strehl ratio and PSF provided by the custom contact lens displayed a clear improvement in the optical quality of the patient's eye.

Figure 3:
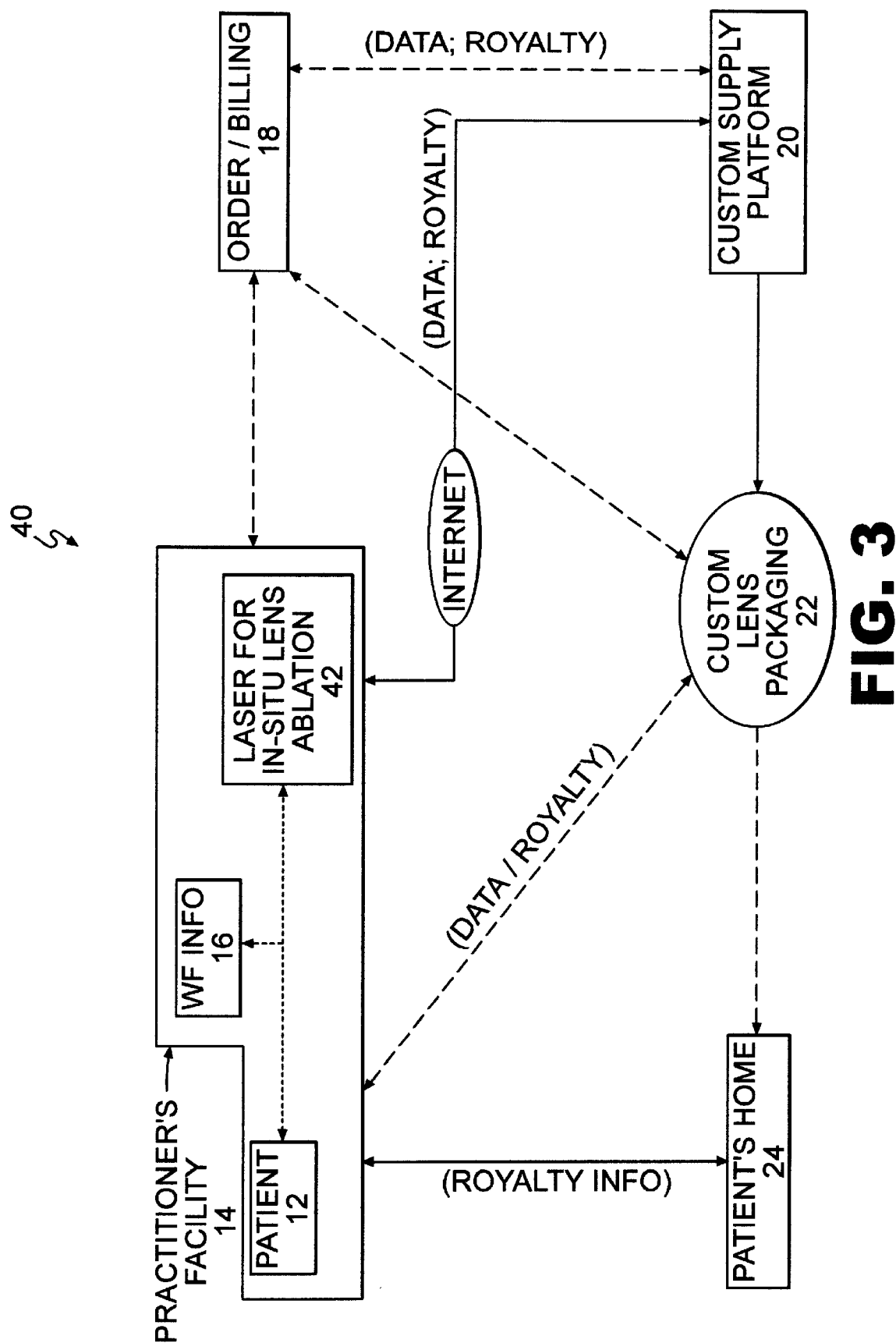
FIG. 3 is a block view of an exemplary in-situ business model according to an embodiment of the invention.

Another embodiment of the invention for providing vision correction to a patient is described in conjunction with an exemplary in-situ business model 40 illustrated schematically in FIG. 3. A patient 12 presents herself in a practitioner's facility 14 where she is fitted with a non-custom trial lens (not shown) including an inlay, an onlay, or a contact lens. A wavefront aberration measurement 16 is obtained and that information is transmitted to an apparatus 42, preferably a laser, suitable for custom shaping of the anterior surface of the trial lens. In an aspect of this embodiment, the wavefront measuring device may be integrated with the laser, but in any event, the laser is located in proximity to the patient such that the anterior lens surface can be custom shaped in-situ. In an aspect of this embodiment, the aberration measurement information 16 is also transmitted in suitable form to a custom lens supply platform 20 where a custom lens is made for the patient. In another aspect of this embodiment, fitting the patient with the trial lens further involves identifying, by a mark or non-contact means, the geometric center of a surface of the trial lens and obtaining the wavefront aberration measurement along an eye axis passing through the geometric center of the lens as described above. In some individual cases, it may be preferable to dilate the patient's pupil to cover an appropriate portion of the optical zone of the trial lens. As described above in connection with the foregoing embodiments of the invention, data transmission protocols, process step segregation into business enterprises with associated contractual rights and revenue streams, and related considerations equally apply to the instant embodiments as though fully set forth per se.

In a further embodiment according to the invention, a patient may engage herself with a diagnostic platform including a wavefront aberration measuring device, without initial practitioner intervention, that is located as a stand-alone platform. The device would be equipped with telecom or datacom capability to accept input and transmit output regarding patient data, ordering data, billing data, etc. to an appropriate respective platform. In addition, the diagnostic platform would be capable of providing the wavefront aberration and, preferably, correction information in a display format suitable for subjective evaluation by the patient. If so desired, the patient could direct the diagnostic platform to transmit the information to a practitioner and/or to a custom contact lens supply platform where a supply of custom contact lenses could be manufactured and packaged, and shipped to the patient or the patient's practitioner. Although this embodiment of the invention engenders an evolving degree of automation, it is not intended to circumvent the inclusion of a practitioner where participation as such is required by state or federal rules, regulations or laws.

Notwithstanding the preferred embodiments specifically illustrated and described herein, it will be appreciated that various modifications and variations of the instant invention are possible in light of the description set forth above and the appended claims, without departing from the spirit and scope of the invention.

We claim:

1. A method for providing vision correction to a patient, comprising:
   a) engaging the patient in a practitioner's facility;
   b) obtaining in said facility a wavefront aberration measurement of an eye of the patient;
   d) providing said wavefront aberration measurement to a custom lens supply platform in a form suitable for input to said supply platform;
   e) producing a customized lens via the supply platform according to data associated with the wavefront aberration measurement; and c) providing said custom lens to the patient or the practitioner.

2. The method according to claim 1, wherein said customized lens is one of a contact lens, an inlay, an onlay, and an IOL.

3. The method according to claim 1, wherein said wavefront aberration measurement is obtained by at least one of a wavefront sensing technique and a corneal topography technique.

4. The method according to claim 1, wherein providing said wavefront aberration measurement to said lens supply platform comprises at least one of voice signals and data signals transmitted over a communication system.

5. The method according to claim 4, wherein said voice or data signals are transmitted over at least one of a land-based and a wireless-based communication system.

6. The method according to claim 1, wherein said lens supply platform is located substantially proximal to said practitioner's facility.

7. The method according to claim 1, wherein said lens supply platform is located substantially remote from said practitioner's facility.

8. The method according to claim 1, wherein producing said lens via the supply platform comprises at least one of laser ablating a surface of a lens, lathing a surface of a lens, cast-molding a surface of a lens, and otherwise machining a surface of a lens.

9. The method according to claim 8, wherein a surface of a lens comprises one of an anterior surface, a posterior surface, and both an anterior and a posterior surface.

10. The method according to claim 1, further comprising obtaining a patient history data.

11. The method according to claim 1, wherein said wavefront aberration measurement includes corneal topography information.

12. The method according to claim 1, further comprising transmitting at least some of the patient data to at least one of an order processing platform and a billing platform.

13. The method according to claim 12, wherein said billing platform is adapted to directly debit a financial account of the patient prior to providing the patient with the custom lens.

14. The method according to claim 12, wherein at least one of said order processing platform and said billing platform is located substantially proximal to at least one of the practitioner's facility and the supply platform.

15. The method according to claim 12, wherein said at least one of the order processing platform and the billing platform is located substantially remote from at least one of the practitioner's facility and the supply facility.

16. The method according to claim 1, wherein providing said custom lens comprises a personalized presentation to said patient.

17. The method according to claim 1, further comprising providing royalty information to a receiving party in response to at least one of the steps (a) through (f).

18. The method according to claim 17, comprising automatically providing said royalty information.

19. A method of providing vision correction to a patient, comprising:
 a) engaging the patient in a practitioner's facility;
 b) obtaining a wavefront aberration measurement from the patient in said practitioner's facility;
 c) transmitting said wavefront aberration measurement to a custom lens supply platform;
 d) manufacturing a custom lens at said supply platform; and
 e) providing said patient with visual performance better than an improved visual performance resulting from a conventional refraction.

20. The method according to claim 19, wherein said custom lens is one of a contact lens, an inlay, an onlay, and an IOL.

21. The method according to claim 19, further comprising segregating steps (b), (c) and (d) into respective businesses (b'), (c') and (d').

22. The method according to claim 21, further comprising providing to another person a contracted right to practice one or more of (b'), (c'), and (d') for consideration.

23. The method according to claim 22, wherein said right is exclusive.

24. The method according to claim 22, wherein said right is non-exclusive.

25. The method according to claim 22, wherein said another person is said practitioner.

26. A method for providing vision correction to a patient, comprising:
 a) engaging the patient in a practitioner's facility;
 b) obtaining a wavefront aberration measurement of the patient's eye;
 d) providing a display of said wavefront aberration measurement in the form of at least one of a picture, a computer simulation, a graphic display, and a mathematical representation of said wavefront.

27. The method according to claim 26, wherein providing said display comprises providing said patient with said display such that said patient may make a subjective evaluation of the wavefront aberration measurement.

28. The method according to claim 26, further comprising transmitting said wavefront measurement to a lens supply platform in a form readable by said lens supply platform for producing a custom lens.

29. The method according to claim 28, wherein said platform comprises at least one of a lens laser ablation system, a lens lathing system, a lens cast-molding system, and a lens machining system.

30. The method according to claim 28, wherein transmitting comprises directly transmitting said data over at least one of a land-based and a wireless communication system.

31. A method for providing vision correction to a patient, comprising:
 a) engaging a patient in a practitioner's facility;
 b) fitting the patient with a trial contact lens having a non-customized anterior surface shape;
 c) providing a mark on said trial lens that identifies a geometric center of a surface of the trial lens;
 d) obtaining a wavefront aberration measurement from the patient's eye along an axis passing through the geometric center of the lens; and
 d) transmitting said aberration measurement to a custom contact lens supply platform.

32. The method according to claim 31 wherein said wavefront measurement comprises corneal topography information.

33. A method for providing vision correction to a patient, comprising:
 a) engaging a patient in a practitioner's facility;
 b) fitting the patient with a trial lens having a non-customized anterior surface shape;
 c) obtaining a wavefront aberration measurement from the patient's eye with the trial lens engaged;
 d) transmitting said aberration measurement to a device adapted for custom-shaping the anterior lens surface; and e) performing in-situ custom shaping of the anterior lens surface via the device.

34. The method according to claim 33, wherein said lens is one of a contact lens, an onlay, and an inlay.

35. The method according to claim 33, further comprising transmitting said aberration measurement to a custom lens supply platform in a form readable by said lens supply platform for producing said lens.

36. The method according to claim 35, wherein said custom lens produced via the lens supply platform is substantially identical at least in surface shape to the custom-shaped in-situ lens.

37. The method according to claim 33 wherein said wavefront aberration measurement comprises corneal topography information.

38. The method according to claim 37 wherein said wavefront aberration measurement is obtained from a device that is linked to at least one of the in-situ lens shaping device and a custom lens supply platform.

39. The method according to claim 38, wherein said lens is one of a contact lens, an onlay, and an inlay.

40. The method according to claim 38, wherein said custom lens supply platform is located substantially remotely from said practitioner's facility.

41. The method according to claim 33, further comprising providing royalty information to a receiving party resulting from the performance of at least one of steps (c) through (e).

42. The method according to claim 41, comprising automatically providing said royalty information.

43. The method according to claim 33, further comprising transmitting at least one of a patient history data and the aberration measurement to at least one of an order processing platform and a billing platform.

44. The method according to claim 43, wherein said billing platform is adapted to directly debit a financial account of the patient prior to providing the patient with the custom lens.

45. The method according to claim 33 wherein the steps of fitting and measuring further comprise:
    providing a mark on said trial lens that identifies a geometric center of a surface of the trial lens prior to custom shaping the anterior surface; and
    measuring the wavefront from the patient's eye along an axis passing through the geometric center of the lens.

46. The method according to claim 45, further comprising dilating the patient's pupil such that it has a size to cover approximately 75% or more of an optical zone of the trial lens.

47. The method according to claim 36, wherein said custom lens is produced by at least one of laser ablating, lathing, machining, and cast-molding a surface of the lens.

48. The method according to claim 38, wherein said custom lens supply platform comprises at least one of a lens laser ablation system, a lens lathing system, and a lens cast-molding system.

49. The method according to claim 45 further comprising custom shaping the anterior surface of the lens in-situ along the measured wavefront axis.

50. A method for providing vision correction to a patient, comprising:
    a) engaging the patient with a device adapted to measure a wavefront aberration of the patient's eye;
    b) providing an output from said device, said output including information about said wavefront aberration, said output further being in a form suitable or adaptable for input to a custom lens supply platform;
    c) transmitting said data to at least one of a practitioner and said lens supply platform;
    d) making said lens via said custom lens supply platform; and
    e) providing the practitioner or the patient with said lens.

51. The method according to claim 50, further comprising providing a display of the aberration measurement to said patient in a form such that said patient may make a subjective evaluation of the measurement.

52. A method for providing vision correction to a patient, comprising:
    measuring an ocular characteristic of the patient's eye wherein said measurement includes at least one of topography data and wavefront aberration data;
    evaluating said measurement, said evaluation producing an option matrix that includes at least a comparison of prospective vision correction as a function of a prospective eye treatment.

53. The method of claim 52, wherein said measurement is normalized for correction of defocus and astigmatism.

54. The method of claim 52, wherein said prospective eye treatment includes a custom lens, a surgical procedure or no treatment.

55. The method of claim 54, further wherein a custom lens treatment is selected by the patient and said selection is automatically input to a custom lens supply platform.

56. The method of claim 55, further comprising obtaining patient history data and patient financial data, and automatically transmitting the financial data to an order/billing platform.

57. The method according to claim 33, wherein obtaining a wavefront aberration measurement includes the further steps of:
    allowing the trial lens to come to a resting position on the patient's eye;
    aligning a visual axis of the patient's eye to a measurement axis of a metrology device that measures the wavefront aberration;
    shifting the measurement axis of the metrology device to an axis that is parallel to the visual axis and which passes through the geometric center of the trial lens; and
    obtaining the wavefront measurement relative to the geometric center of the lens.

58. A method for providing vision correction to a patient, comprising:
    a) engaging a patient in a practitioner's facility;
    b) fitting the patient with a trial lens having a non-customized anterior surface shape;
    c) allowing the trial lens to come to a resting position on the patient's eye;
    d) aligning a visual axis of the patient's eye to a measurement axis of a metrology device that measures a wavefront aberration measurement of the eye;
    e) shifting the measurement axis of the metrology device to an axis that is parallel to the visual axis and which passes through the geometric center of the trial lens; and
    f) obtaining the wavefront aberration measurement relative to the geometric center of the trial lens.

59. The method of claim 58, further comprising the step of transmitting said aberration measurement to a device adapted for custom-shaping the anterior lens surface.

* * * * *